United States Patent
Pilloni et al.

(10) Patent No.: US 9,732,369 B2
(45) Date of Patent: Aug. 15, 2017

(54) METHOD FOR SELECTIVE TREATMENT OF MICROBIOLOGICALLY INFLUENCED CORROSION (MIC) OF METAL SURFACES

(71) Applicants: Giovanni Pilloni, Jersey City, NJ (US); Dennis R. Enning, Houstin, TX (US)

(72) Inventors: Giovanni Pilloni, Jersey City, NJ (US); Dennis R. Enning, Houstin, TX (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 114 days.

(21) Appl. No.: 14/809,444

(22) Filed: Jul. 27, 2015

(65) Prior Publication Data

US 2017/0030508 A1    Feb. 2, 2017

(51) Int. Cl.
| | |
|---|---|
| *B05D 7/22* | (2006.01) |
| *B05D 3/00* | (2006.01) |
| *C12Q 1/06* | (2006.01) |
| *C12Q 1/68* | (2006.01) |
| *C23F 15/00* | (2006.01) |
| *C09K 8/54* | (2006.01) |
| *G01N 17/00* | (2006.01) |
| *F16L 58/04* | (2006.01) |
| *B08B 9/055* | (2006.01) |

(52) U.S. Cl.
CPC .............. *C12Q 1/06* (2013.01); *B05D 3/002* (2013.01); *B05D 7/222* (2013.01); *C09K 8/54* (2013.01); *C12Q 1/689* (2013.01); *C23F 15/00* (2013.01); *G01N 17/008* (2013.01); *B08B 9/055* (2013.01); *F16L 58/04* (2013.01)

(58) Field of Classification Search
CPC . F16L 58/04; B08B 9/055; C12Q 1/06; B05D 7/22; B05D 7/222; B05D 3/002
USPC .......................................................... 427/230
See application file for complete search history.

(56) References Cited

U.S. PATENT DOCUMENTS

| | | | |
|---|---|---|---|
| 6,109,829 | A  | 8/2000  | Cruickshank |
| 6,182,761 | B1 | 2/2001  | Bednar |
| 6,874,757 | B2 | 4/2005  | Hallett |
| 7,275,564 | B2 | 10/2007 | Bazin et al. |
| 7,739,767 | B2 | 6/2010  | Galloway |
| 8,719,989 | B1 | 5/2014  | Qanaei |
| 8,858,732 | B1 | 10/2014 | Al Qanaei |

(Continued)

OTHER PUBLICATIONS

Li, Kwan et al., "Beating the bugs: Roles of microbial biofilms in corrosion," 2013, Corrosion Reviews, vol. 31, Issue 3-6, pp. 73-84.

(Continued)

*Primary Examiner* — Kirsten Jolley
(74) *Attorney, Agent, or Firm* — Robert A. Migliorini

(57) ABSTRACT

Provided is a multi-phase process for conditionally treating MIC by evaluating whether MIC-correlating conditions exist, the degree of MIC, if present, and then applying a concomitant MIC-mitigating treatment which is adjusted in its degree of aggressiveness in proportion to MIC severity. The disclosed methodology allows, in part, for the continuous or periodic monitoring and assessment of MIC risk in petroleum-based equipment (e.g., pipeline) and the administering of a treatment that corresponds to the level of severity of the MIC resulting in a more fine-tuned, localized, and cost-effective treatment.

25 Claims, 2 Drawing Sheets

(56) References Cited

U.S. PATENT DOCUMENTS

| | | | |
|---|---|---|---|
| 9,010,826 B1 | 4/2015 | Osborne | |
| 2003/0085136 A1* | 5/2003 | Marchal | G01N 17/02 |
| | | | 205/775.5 |
| 2005/0006250 A1* | 1/2005 | Russell | G01N 17/043 |
| | | | 205/725 |
| 2015/0021269 A1* | 1/2015 | Enning | C09K 8/605 |
| | | | 210/663 |

OTHER PUBLICATIONS

Enning, Dennis et al., "Corrosion of Iron by Sulfate-Reducing Bacteria: New Views of an Old Problem," Applied and Environmental Microbiology, 2014, vol. 80, Issue 4, pp. 1226-1236.

Kato, Souichiro et al., "Isolation of Acetogenic Bacteria That Induce Biocorrosion by Utilizing Metallic Iron as the Sole Electron Door," Applied and Environmental Microbiology, 2015, vol. 81, Issue 1, pp. 67-73.

Paisse, S. et al., "Sulfate-reducing bacteria inhabiting natural corrosion deposits from marine steel structures," Applied Microbiology and Biotechnology, 2013, vol. 97, Issue 16.

Mand, J. et al., "The role of acetogens in microbially influenced corrosion of steel," Frontiers in Microbiology, 2014, vol. 5, Article No. 268.

ASM Handbook Volume 11: Failure and Analysis Prevention, Shipley, R.J. and Becker, W.T. (eds), 2014, ASM International, pp. 881-898.

Kip, N. et al., "The dual role of microbes in corrosion," The International Society for Microbial Ecology, 2015, vol. 9, Issue 3, pp. 542-551.

Lee, W. et al., "Role of sulfate-reducing bacteria in corrosion of mild-steel—a review," 1995, Biofouling, vol. 8, Issue 3, pp. 165-194.

\* cited by examiner

METHOD FOR SELECTIVE TREATMENT OF MICROBIOLOGICALLY INFLUENCED CORROSION (MIC) OF METAL SURFACES

FIELD

The disclosure generally relates to an effective and cost-effective solution to better mitigate microbiologically influenced corrosion ("MIC") of solid surfaces, such as the equipment used by the petroleum and natural gas industries to store, transport, and process raw materials such as oil and gas. More specifically, the disclosure relates to methods for continuous or periodic monitoring and assessment of MIC risk in petroleum-based equipment and the administering of appropriate treatment programs which correspond to the level of MIC severity. Accordingly, the disclosure further relates to a method for MIC mitigation that involves the assessment and monitoring of various physical and biological parameters as indicators of MIC conditions paired with concomitant treatment programs that match the MIC conditions identified.

BACKGROUND

Microbiologically influenced corrosion ("MIC") poses severe operational, environmental, and safety problems to the petroleum and/or natural gas industries, particularly with respect to corrosion of equipment used in the storage, processing, and/or transport of oil and gas crude and/or processed materials. Costs resulting from MIC in these industries due to repair and replacement of damaged equipment, spoiled oil, environmental clean-up, and injury-related health care, amount to well over several billion USD per year.

The mechanisms by which microbial influenced corrosion causes damage are poorly understood despite many decades of research. See Kwan Li et al., "Beating the bugs: Roles of microbial biofilms in corrosion, Corrosion Reviews," Vol. 31, Issue 3-6, December 2013, pp. 73-84 (the contents of which are incorporated by reference). However, it is believed that microbiologically influenced corrosion is primarily caused by the formation of microbial biofilms on equipment metal surfaces that come into contact with produced water associated with crude oil and gas and/or the liquid systems involved in their refinery.

The microorganisms thought to be primarily responsible for corrosion at least in an anaerobic environment within the oil industry are sulfate-reducing bacteria. Other culpable bacteria include iron oxidizing bacteria, sulfur oxidizing bacteria, nitrate reducing bacteria, methanogens, and acid producing bacteria, among others. These categories of bacteria generally are capable of oxidizing metal directly, producing metabolic products that are corrosive (e.g., hydrogen sulfide gas), and/or leading to the formation of biofilms that otherwise alter the local environment thereby accelerating corrosion. See Jack, T. R. (2002) Biological corrosion failures. In ASM Handbook Volume 11: Failure Analysis and Prevention. Shipley, R. J., and Becker, W. T. (eds). Materials Park, Ohio, USA: ASM International, pp. 881-898 and Enning and Garrelfs (2014) Corrosion of iron by sulfate-reducing bacteria—New views of an old problem. Applied and Environmental Microbiology. Volume 80, pp. 1226-1236.

Sulfate-reducing bacteria, are ubiquitous and can grow in almost any environment. They are routinely found in waters associated with oil production systems and can be found in virtually all industrial aqueous processes, including cooling water systems and petroleum refining. Sulfate-reducing bacteria require an anaerobic (oxygen-free) aqueous solution containing adequate nutrients, an electron donor, and electron acceptor. A typical electron acceptor is sulfate, which produces hydrogen sulfide upon reduction. Hydrogen sulfide is a highly corrosive gas and reacts with metal surfaces to form insoluble iron sulfide corrosion products. In addition, hydrogen sulfide partitions into the water, oil, and natural gas phases of produced fluids and creates a number of serious problems. For instance, "sour" oil and gas, which contains high levels of hydrogen sulfide, have a lower commercial value than low sulfide oil and gas. Removing biogenic hydrogen sulfide from sour oil and gas increases the cost of these products. It is also an extremely toxic gas and is immediately lethal to humans at even small concentrations. Thus, its presence in the oil field poses a threat to worker safety.

Corrosion—often characterized in association with pitting of metal surfaces—caused by sulfate-reducing bacteria or other environmental microorganisms frequently results in extensive damage to oil and gas storage, production, and transportation equipment. Pipe systems, tank bottoms, and other pieces of oil production equipment can rapidly fail if there are areas where microbial corrosion is occurring. If a failure occurs in a pipeline or oil storage tank bottom, the released oil can have serious environmental consequences. Also, if a failure occurs in a high pressure water or gas line, the consequences may be worker injury or death. Any failure at least involves repair or replacement costs.

A variety of strategies have been developed or discussed to mitigate the corrosive effects of MIC and/or the biofilms that contribute to or cause MIC. Such techniques include the use of corrosion-resistant metals, temperature control, pH control, radiation, filtration, protective coatings, the use of corrosion inhibitors or other chemical controls (e.g., biocides, oxidizers, acids, alkalis), bacteriological controls (e.g., phages, enzymes, parasitic bacteria, antibodies, competitive microflora), pigging (i.e., mechanical delamination of corrosion products), anodic and cathodic protection, and modulation of nutrient levels. However, each of these existing methods face obstacles, such as, high cost, lack of effectiveness, short life-span, or requirement for repeat applications. Moreover, given the highly unpredictable nature of MIC formation, it is challenging to know just when to administer such treatments, as well as what level of aggressiveness any given treatment should have. A more thorough understanding of the conditions which lead to MIC formation would allow improved MIC mitigation management since treatments could be more localized and selective. This would also lead to significant cost savings as treatments would not be wasted on componentry that lack the conditions conducive for MIC formation.

Thus, there exists a need in the art for an improved approaches for MIC mitigation that facilitate reliable prediction, assessment, and monitoring of MIC conditions paired with treatment programs which are matched to the level of MIC severity.

SUMMARY

The disclosure relates, in part, to the surprising discovery that certain physical and biological parameters associated with microbiologycally influenced corrosion (MIC) showed a constant positive correlation with severity of measured corrosion and can be used not only to predict conditions leading to MIC, but could also be used to monitor and/or assess MIC formation in a manner that drives the selection and implementation of appropriately aggressive treatments for MIC mitigation. The disclosed methods allow for the reliable prediction of conditions leading to MIC in various equipment involved in storing (e.g., tanks), transporting (e.g., pipeline), and refining petroleum materials. The methods herein further allow for the selection of and application of a range of treatments having differing levels of aggressiveness.

In further aspects, the disclosure reflects the unexpected findings that certain correlations exist between physical parameters, such as, temperature, pH, and flow rate, as well as biological parameters, such as, cell biomass and the microbial community composition, and the existence of conditions that are suitable or which reliably correlate with the formation of MIC. Based on these new findings, the inventors have devised a multi-phase process for conditionally treating MIC by evaluating whether MIC-correlating conditions exist, the degree of MIC, if present, and then applying concomitant MIC-mitigating treatment scheme, which is adjusted in its degree of aggressiveness in proportion to MIC severity. The disclosed methodology allows, in part, for the continuous or periodic monitoring and assessment of MIC susceptibility in petroleum-based equipment (e.g., pipeline) and the administering of a treatment that corresponds to the level of severity of MIC. The methodology also provides for continuous or periodic assessment to evaluate the effectiveness of said treatments, and whether reductions and/or increases in the aggressiveness of the treatment are required. The schemes described herein provide for selective MIC management which in turn results in more effective and targeted solutions for improved materials integrity management with the additional benefit of potentially significant costs savings from more effective use of MIC control measures such as biocide application.

In certain aspects, the description provides a method for predicting whether MIC-forming conditions exist comprising measuring at least one parameter predictive of MIC-forming conditions.

In a further aspect, the description provides a system for predicting whether MIC-forming conditions exist comprising a non-transitory computer readable configured to execute a method as described herein.

In another aspect, the description relates to a method of MIC mitigation comprising (a) measuring at least one parameter predictive of MIC-forming conditions, (b) determining the level of severity of existing MIC, and (c) administering a concomitant MIC mitigation treatment that is proportional to the level of MIC severity.

In an additional aspect, the description provides a system for MIC mitigation comprising a non-transitory computer readable configured to execute a method of MIC mitigation as described herein. In certain embodiments, the system is configured to execute a treatment process in response to the output of the measuring and determining steps as described herein.

In certain embodiments, at least one parameter predictive of MIC-forming conditions is selected from the group consisting of temperature, pH, flow rate, water drop-out, planktonic cell count, and microbial composition.

In certain other embodiments, at least two parameters are tested, one of which is temperature.

In some embodiments, a temperature that is below about 60° C. is predictive of MIC-forming conditions. In other embodiments, a temperature that is below about 70° C., or more preferably that is below about 80° C., or more preferable that is lower than about 90° C. is predictive of MIC-forming conditions. In still other embodiments, a temperature between about 20-40° C. is predictive of MIC-forming conditions. In still other embodiments, a temperature that is above about 60° C. correlates with conditions that do not support MIC. In yet other embodiments, a temperature that is above about 80° C. correlates with conditions that do not support MIC. In still other embodiments, a temperature that is above about 90° C. correlates with conditions that do not support MIC.

In certain other embodiments, at least two parameters are tested, one of which is the quantity of microbial biomass, e.g., bacteria or archaea, present. The biomass can be measured as the quantity or concentration of planktonic bacteria. The biomass can also be measured as the quantity or concentration or density of bacteria in a biofilm. The biomass can be measured by any known means, such as by quantitative PCR, ATP (adenosine triphosphate) assay, or serial dilution technique (SD). In certain embodiments, the biomass is measured in terms of microbial equivalents (ME, which is comparable to cell numbers). In some embodiments, the MIC-forming conditions require at least $5\times10^5$ microbial equivalents per $cm^2$ of biofilm. In other embodiments, MIC-forming conditions require at least $1\times10^3$ cells per ml (planktonic cell counts) as measured by ATP assay or qPCR, or at least $1\times10^2$ cells per ml (planktonic cell counts) as measured by SD assay.

In certain other embodiments, the level of severity of existing MIC is monitored by measuring the quantity of biofilm biomass and/or observing the metal surfaces (e.g., in situ or of test coupons) for evidence of corrosion (e.g., visible pitting) and corrosion-related debris.

In certain embodiments, the level of severity of existing MIC is lowest (i.e., level 1 severity) when the biofilm biomass is lower than a threshold, wherein the threshold can be $1\times10^2$ cells per $cm^2$, $1\times10^3$ cells per $cm^2$, or $1\times10^4$ cells per $cm^4$. Preferably, the threshold is $1\times10^4$ cells per $cm^4$ when the biomass is determined by ATP assay or quantitative PCR, but can be $1\times10^2$ cells per $cm^2$ when the biomass is determined by SD assay.

In other embodiments, the severity is increased (i.e., level 2) if the quantity of biofilm biomass is above the threshold but there are no visible signs of localized corrosion (e.g., no visible pitting on in situ components or on coupons).

In still other embodiments, the severity is increased yet again (i.e., level 3) if the quantity of biofilm is above the threshold, and there are visible signs of localized corrosion (e.g., visible pitting on in situ components or on coupons), but the measured level of corrosion on coupons is less than 1 milli-inch per year (<1 mpy).

In still further embodiments, the severity is increased still again (i.e., level 4) if the quantity of biofilm is above the threshold, and there are visible signs of localized corrosion (e.g., visible pitting on in situ components or on coupons), and the measured level of corrosion on coupons is more than 1 milli-inch per year (>1 mpy), but there is no evidence of visible corrosion-related debris.

In still another embodiment, the severity is increased yet again (i.e., level 5) if the quantity of biofilm is above the threshold, and there are visible signs of localized corrosion (e.g., visible pitting on in situ components or on coupons), and the measured level of corrosion on coupons is more than 1 milli-inch per year (>1 mpy), and there is evidence of visible corrosion-related debris.

In accordance with an additional embodiment, the disclosed method further involves (c) administering a concomitant MIC mitigation treatment that is proportional to the level of MIC severity. Preferably, as the severity of the MIC is increased, the degree of aggressiveness of the MIC treatment is also increased.

In various embodiments, the MIC treatment is a singular type of treatment, e.g., a biocide injection, or a pigging treatment. However, in other embodiments, the MIC treatment is a combination treatment involving one or more types of treatments, e.g., a combination of a biocide injection and a pigging treatment.

The level of aggressiveness of any given treatment or combination treatment will depend on a number of different factors, such as, but not limited to: (a) frequency of administration (e.g., number of times per day, number of times per week, number of times per month), (b) quantity of administration, (c) whether treatment is singular (generally less aggressive) or in combination with one or more additional treatments (generally more aggressive). It will be further appreciated that a variety of factors may impact how any particular treatment is administered such that a desired final concentration or amount of treatment is presented to the target environment being treated, such as, in the case of a pipeline, the flowrate, pipe volume, temperature, pH, and the composition of the bacterial community.

In certain embodiments, the treatment is a first-level treatment (lowest level or degree of aggressiveness) comprising administering a biocide to provide a final concentration at the site of interest of 5-1000 ppm over the course of 10 minutes to 10 hours every 14-28 days in combination with pigging at least twice per year.

In other embodiments, the treatment is a second-level treatment comprising administering a biocide to provide a final concentration at the site of interest of 5-1000 ppm over the course of 10 minutes to 10 hours every 7-14 days in combination with pigging every 4-8 weeks.

In still other embodiments, the treatment is a third-level treatment comprising administering a biocide to provide a final concentration at the site of interest of 5-1000 ppm over the course of 10 minutes to 10 hours every 3-7 days in combination with pigging every 2-4 weeks.

In still further embodiments, the treatment is a fourth-level treatment comprising administering a biocide to provide a final concentration at the site of interest of 5-1000 ppm over the course of 10 minutes to 10 hours every 3-7 days in combination with pigging every week.

In another aspect, the disclosure relates to a method for selectively mitigating or treating microbiologically influenced corrosion (MIC) of a site of interest comprising: a) determining whether suitable conditions for MIC exist at the site of interest; b) if so, monitoring the degree of MIC severity at the site of interest; c) administering a MIC treatment to the site of interest that corresponds to the degree of MIC severity; wherein the determining step comprises at least measuring the temperature at the site of interest, and wherein the monitoring step comprises at least measuring biofilm biomass at the site of interest.

The determining step (a) of the third aspect can comprise measuring the temperature, pH, flow rate, water drop-out, planktonic cell count, and microbial composition to determine whether suitable conditions exist at the site of interest for MIC.

The monitoring step (b) can comprise measuring the biofilm biomass and characterizing the level of corrosion at the site of interest to determine the degree of MIC.

The treatment step can comprise administering a MIC treatment to the site of interest that is proportional to the degree of MIC, wherein the MIC treatment comprises a combination of biocide application and pigging.

In certain embodiments, the determining step (a) can comprise:

(i) measuring the temperature at the site of interest, wherein if the temperature is greater than a threshold temperature, then suitable conditions for MIC do not exist and treatment is not required, but if the temperature is less than the threshold temperature, then proceed to (ii) measuring the pH at the site of interest, wherein if the pH falls outside a threshold pH range, then suitable conditions for MIC do not exist and treatment is not required, but if the pH falls within a threshold pH range, then proceed to (iii) measuring the flow rate at the site of interest and the water drop-out, wherein if the flow rate is greater than a threshold flow rate and there is no water drop-out, then suitable conditions for MIC do not exist and treatment is not required, but if the flow rate is less than the threshold flow rate and there is water drop-out, then proceed to (iv) measuring the planktonic cell count at the site of interest, wherein if planktonic cell count is below a threshold cell count, then suitable conditions for MIC do not exist and treatment is not required, but if the planktonic cell count is above a threshold cell count, then proceed to (v) determining the microbial community at the site of interest, wherein if less than a threshold percent of the total sessile microbial population comprises species associated with MIC, then suitable conditions for MIC do not exist and treatment is not required, but if more than the threshold percent of the total microbial population comprises species associated with MIC, then proceed to the monitoring step (b) of claim 1 to determine the degree of MIC, and the corresponding treatment of step (c).

In certain embodiments, the threshold temperature of (i) is 60° C.

In certain other embodiments, the threshold temperature of (i) is 90° C.

In other embodiment, the threshold pH range of (ii) is a pH of 4-12.

In still other embodiments, the threshold flow rate of (iii) is 10 meters per second (m/s).

In yet another embodiment, the threshold cell count is $10^3$ cells per ml if the cell count is determined by an ATP assay.

In other embodiments, the threshold cell count is $10^2$ cells per ml if the cell count is determined by an SD assay.

In still other embodiments, the threshold cell count is $10^3$ cells per ml if the cell count is determined by an qPCR assay.

In certain embodiments of the third aspect, the monitoring step (b) comprises:

(i) measuring the biofilm biomass at the site of interest, wherein if the biofilm biomass is below a threshold biomass, then a first-level MIC treatment is administered to the site of interest, but if the measured biofilm biomass is above the threshold biomass, then proceed to (ii) detecting or investigating the site of interest for localized corrosion, wherein if there is no localized corrosion at the site of interest, then a second-level MIC treatment is administered to the site of interest, but if there is localized corrosion, then proceed to (iii) measuring the level of corrosion of one or more coupons, wherein if the level of corrosion is below a threshold level, then a third-level MIC treatment is administered to the site of interest, but if the level of corrosion is above the threshold level, then proceed to (iv) detecting the presence of corrosion debris at the site of interest, wherein if no debris is present, then the third-level MIC treatment is administered, but if debris is detected then a fourth-level MIC treatment is administered;

wherein the aggressiveness of the first-level MIC treatment is lower than the second-level MIC treatment, which is lower than the third-level MIC treatment, which is lower than the fourth-level MIC treatment.

In some embodiments, the threshold biomass of (i) is $10^4$ cells/cm$^2$ if measured by an ATP assay, or $10^2$ cells/cm$^2$ if measured by an SD assay, or $10^4$ cells/cm$^2$ if measured by a qPCR assay.

In other embodiments, the localized corrosion of (ii) comprises corrosion-related pitting.

In still other embodiments, the threshold level of corrosion of (iii) is 1 milli-inch per year.

In another aspect, the first-level treatment can comprise administering a biocide to provide a final concentration at the site of interest of 5-1000 ppm over the course of 10 minutes to 10 hours every 14-28 days in combination with pigging at least twice per year. The second-level treatment can comprise administering a biocide to provide a final concentration at the site of interest of 5-1000 ppm over the course of 10 minutes to 10 hours every 7-14 days in combination with pigging every 4-8 weeks. The third-level treatment can comprise administering a biocide to provide a final concentration at the site of interest of 5-1000 ppm over the course of 10 minutes to 10 hours every 3-7 days in combination with pigging every 2-4 weeks. The fourth-level treatment can comprise administering a biocide to provide a final concentration at the site of interest of 5-1000 ppm over the course of 10 minutes to 10 hours every 3-7 days in combination with pigging every week.

In certain embodiments, the MIC is caused by a bacterial or archaea biofilm deposited on the surface of the site of interest.

The bacterial biofilm can be formed by anaerobic bacteria, which can be selected from the group consisting of sulfate-reducing bacteria, sulfur- or thiosulfate-reducing bacteria, iron-oxidizing bacteria, sulfur-oxidizing bacteria, nitrate-reducing bacteria, methanogens, and acid producing bacteria.

The sulfate-reducing bacteria can be of the genera *Desulfuvibrio, Desulfotomaculum, Desulfosporomusa, Desulfosporosinus, Desulfobacter, Desulfobacterium, Desulfobacula, Desulfobotulus, Desulfocella, Desulfococcus, Desulfofaba, Desulfofrigus, Desulfonema, Desulfosarcina, Desulfospira, Desulfotalea, Desulfotignum, Desulfobulbus, Desulfocapsa, Desulfopila, Desulfofustis, Desulforhopalis, Desulfoarculus, Desulfobacca, Desulfomonile, Desulfotigmum, Desulfohalobium, Desulfomonas, Desulfonatronovibrio, Desulfomicrobium, Desulfonatronum, Desulfacinum, Desulforhabdus, Syntrophobacter, Syntrophothermus, Thermaerobacter, Thermodesulforhabdus*, or any other member of the sulfate-reducing bacteria The sulfate-reducing bacteria can be the genera *Desulfuvibrio*.

In various embodiments, the site of interest is a metal surface of equipment for refining, storing, or transporting of crude or processed oil.

In other embodiments, the site of interest is a metal surface of equipment for refining, storing, or transporting of natural gas.

The biocide used in certain embodiments can be selected from the group consisting of germicides, antibiotics, antibacterials, antivirals, antifungals, antiprotozoals and antiparasites or combinations thereof.

In certain other embodiments, the disclosed methods can include a secondary treatment for mitigating or eliminating MIC selected from the group consisting of pigging, radiation treatment, pH adjustment, nutrient adjustment, and installation of corrosion-resistant metals.

In various embodiments, the susceptible metal surface that is treated is a metal surface of equipment for refining, storing, or transporting of crude or processed oil or gas, and can include, for example, metal (e.g., steel) pipelines, storage containers, or refinery processing equipment.

In still other embodiments, the biocides used herein may be provided in a liquid composition having an acidic pH, ranging from about 6.0-7.0, to about 5.5-6.5, to about 4.5-5.5, to about 3.5-4.5, to about 2.5-3.5, to about 1.5-2.5, or lower than 1.5.

In still other embodiments, the biocides used herein may be provided in a liquid composition having an alkaline pH, ranging from about 7.0-7.5, to about 7.5-8.5, to about 8.5-9.5, to about 9.5-10.5, to about 10.5-11.5, to about 11.5-12.5, to about 12.5-13.5 to about 14.

In certain other embodiments, the pH of the aqueous environment surrounding or at the metal surface to be treated can be adjusted with buffers or other pH-altering agents to adjust the pH to any basic, neutral, or acidic conditions.

In still other embodiments, the biocides used in the disclosed treatments may be selected from the group consisting of germicides, antibiotics, antibacterials, antivirals, antifungals, antiprotozoals and antiparasites, or from combinations thereof.

In other embodiments, the disclosed treatment methods may include or involve a secondary or co-treatment for mitigating or eliminating microbiologically influenced corrosion of the metal surface selected from the group consisting of pigging, radiation treatment, pH adjustment, nutrient adjustment, and installation of corrosion-resistant metals.

In various embodiments, the effective amount of the liquid composition comprising the disclosed biocides provides a concentration of the biocide that is between about 50-500 micromolar, about 0.5-1.0 mM, about 1.0 mM-5 mM, about 2.5 mM-10 mM, about 5 mM-25 mM, about 10 mM-100 mM, or about 50 mM-1000 mM.

Where applicable or not specifically disclaimed, any one of the embodiments described herein are contemplated to be able to combine with any other one or more embodiments, even though the embodiments are described under different aspects of the disclosure. These and other embodiments are disclosed or are obvious from and encompassed by, the following Detailed Description, including the Drawings and Examples herein.

BRIEF DESCRIPTION OF THE DRAWINGS

The following detailed description, given by way of example, but not intended to limit the disclosure solely to the specific embodiments described, may best be understood in conjunction with the accompanying drawings.

DETAILED DESCRIPTION

Figure 1:
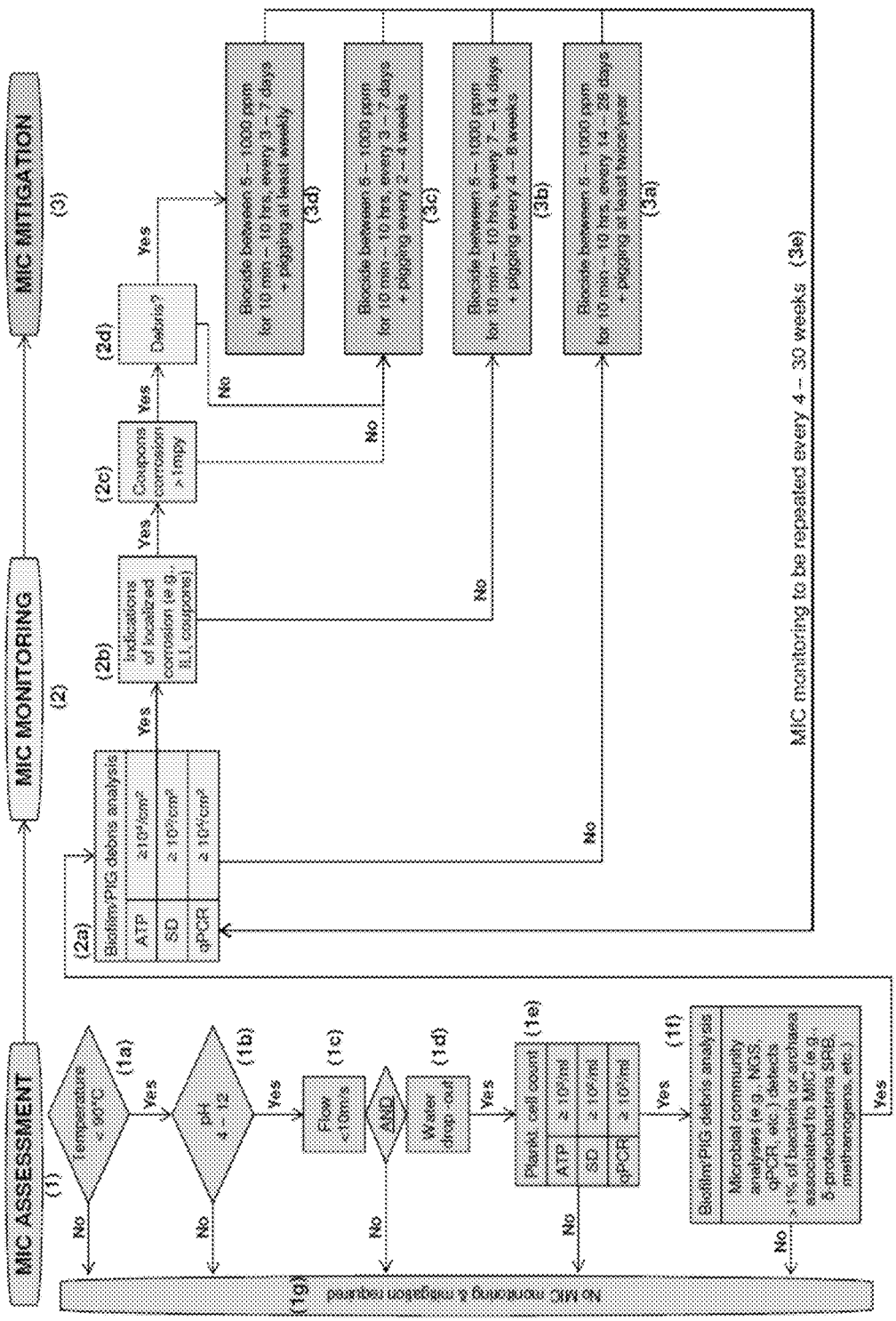
FIG. 1 depicts a the proposed framework for the selective MIC treatment of petroleum equipment, e.g., pipeline, as disclosed further in Example 2 and which is organized into three separate phases or modules: MIC assessment (phase 1), MIC monitoring (phase 2), and MIC mitigation (phase 3).

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the disclosure.

Microbiologically Influenced Corrosion ("MIC")—at term of art—is frequently observed at oil production sites and in transport pipelines, among other types of equipment involved in the oil and gas production industry. MIC poses severe operational, environmental, and safety problems to the petroleum and/or natural gas industries, particularly with respect to corrosion of equipment used in the storage, processing, and/or transport of oil and gas crude and/or processed materials. Costs resulting from MIC in these industries due to repair and replacement of damaged equipment, spoiled oil, environmental clean-up, and injury-related health care, amount to well over several billion USD per year. Biofilms that form on the surfaces of such metal components are thought to be the primary causative agent triggering such corrosion as many biofilm-forming environmental bacteria—particularly those in anaerobic environments—produce harmful gases (e.g., hydrogen sulfide), acids (e.g., sulfuric acid), and other agents which are highly corrosive, in addition to directly affecting materials integrity. Hydrogen sulfide also poses health and safety concerns to workers in the industry. Current mitigation techniques to reduce MIC are available, but are not effective enough and/or are not practical in the industry due to high cost and because conditions that lead to MIC formation are not well understood or predictable based on current knowledge.

The disclosure relates, in part, to the surprising discovery that certain physical and biological parameters associated with microbiologically influenced corrosion (MIC) showed a constant positive correlation with severity of measured corrosion and could be used not only to predict conditions leading to MIC, but could also be used to monitor and/or assess MIC formation in a manner that drives the selection and implementation of appropriately aggressive treatments for MIC mitigation. The disclosed methods allow for the reliable prediction of conditions leading to MIC in various equipment involved in storing (e.g., tanks), transporting (e.g., pipeline), and refining petroleum materials. The methods herein further allow for the selection of and application of a range of treatments having differing levels of aggressiveness.

It has been discovered that certain correlations exist between physical parameters, such as, temperature, pH, and flow rate, as well as biological parameters, such as, planktonic cell biomass and the microbial community composition, and the existence of conditions that are suitable or which reliably correlate with the formation of MIC. Based on these findings, the inventors have devised a multi-phase process for conditionally treating MIC by evaluating whether MIC-correlating conditions exist, the degree of MIC, if present, and then applying concomitant MIC-mitigating treatment scheme which adjusted in its degree of aggressiveness in proportion to MIC severity. The disclosed methodology allows, in part, for the continuous or periodic monitoring and assessment of MIC risk in petroleum-based equipment (e.g., pipeline) and the administering of a treatment that corresponds to the level of severity of MIC. The methodology also provides for continuous or periodic assessment to evaluate the effectiveness of said treatments, and whether reductions and/or increases in the aggressiveness of the treatment are required. The schemes described herein provide for selective MIC management which in turn results in more effective and targeted solutions with significant costs savings.

The following is a detailed description of the disclosure provided to aid those skilled in the art in practicing the present disclosure. Those of ordinary skill in the art may make modifications and variations in the embodiments described herein without departing from the spirit or scope of the present disclosure. Unless otherwise defined, all technical and scientific terms used herein have the same meaning as commonly understood by one of ordinary skill in the art to which this disclosure belongs. The terminology used in the description of the disclosure herein is for describing particular embodiments only and is not intended to be limiting of the disclosure. All publications, patent applications, patents, figures and other references mentioned herein are expressly incorporated by reference in their entirety.

Although any methods and materials similar or equivalent to those described herein can also be used in the practice or testing of the present disclosure, the preferred methods and materials are now described. All publications mentioned herein are incorporated herein by reference to disclose and described the methods and/or materials in connection with which the publications are cited.

Unless defined otherwise, all technical and scientific terms used herein have the meaning commonly understood by a person skilled in the art to which this disclosure belongs. The following references, the entire disclosures of which are incorporated herein by reference, provide one of skill with a general definition of many of the terms (unless defined otherwise herein) used in this disclosure: Singleton et al., Dictionary of Microbiology and Molecular Biology ($2^{nd}$ ed. 1994); The Cambridge Dictionary of Science and Technology (Walker ed., 1988); The Glossary of Genetics, $5^{th}$ Ed., R. Rieger et al. (eds.), Springer Verlag (1991); and Hale & Marham, the Harper Collins Dictionary of Biology (1991). Generally, the procedures of molecular biology methods described or inherent herein and the like are common methods used in the art. Such standard techniques can be found in reference manuals such as for example Sambrook et al., (2000, Molecular Cloning—A Laboratory Manual, Third Edition, Cold Spring Harbor Laboratories); Ausubel et al., (1994, Current Protocols in Molecular Biology, John Wiley & Sons, New-York); and Methods in Molecular Biology, Volume 733, 2011, High-Throughput Next Generation Sequencing, Methods and Applications Ed. Y. M. Kwon and S. C. Ricke, Springe.

The following terms may have meanings ascribed to them below, unless specified otherwise. However, it should be understood that other meanings that are known or understood by those having ordinary skill in the art are also possible, and within the scope of the present disclosure. All publications, patent applications, patents, and other references mentioned herein are incorporated by reference in their entirety. In the case of conflict, the present disclosure, including definitions, will control. In addition, the materials, methods, and examples are illustrative only and not intended to be limiting.

As used herein, the singular forms "a", "and", and "the" include plural references unless the context clearly dictates otherwise. All technical and scientific terms used herein have the same meaning.

As used herein, the term "biocide" refers to a chemical or biological substance which can deter, render harmless, or exert a controlling effect on any harmful organism by chemical or biological means. Biocides include those that are synthetic, but also those which are naturally obtained, e.g., obtained or derived from bacteria and plants. Biocides can include, but are not limited to, germicides, antibiotics, antibacterials, antivirals, antifungals, antiprotozoals and antiparasites, or combinations thereof. Such compounds are well-known in the art and may be obtained easily from commercial sources. Reference may be made to the biocides disclosed in the book *Corrosion in the Petrochemical Industry*, Ed. Linda Garverick, ASM International, 1994, the contents of which are incorporated herein by reference.

As used herein, the term "Microbiologically Influenced Corrosion" or "MIC" or similar terms are terms in the art and shall be understood according to the meaning ascribed in the field, i.e., corrosion to metal surfaces caused directly or indirectly through the effects of bacteria and their by-products and metabolites at metal surfaces, including especially bacteria that grow on the surface of metal in a biofilm. MIC can occur in both aerobic and anaerobic conditions and generally is thought to require the presence of bacteria in a biofilm. MIC is considered "biotic corrosion." MIC is often associated with surface pitting, which leads to more rapid corrosive failure than uniform corrosion.

As used herein, the term "sulfate-reducing bacteria" or "SRB," which are considered one of the main culprits of biotic corrosion in anaerobic conditions, are a grouping of bacteria that includes at least 220 species which produce $H_2S$, and use sulfates as the terminal electron acceptor. Many SRB are considered obligate anaerobes, meaning that the cells cannot metabolize and/or replicate in the presence of oxygen, although many species can temporarily tolerate low levels of oxygen. Furthermore, anaerobic conditions capable of supporting SRB growth can be created in overall aerobic environments, due to the microniches created within the bacterial biofilm/corrosion product layer. Although SRB are the most studied and well understood of the anaerobic corrosion inducing bacteria, MIC can occur in anaerobic conditions in the absence of SRB.

As used herein, the term "corrosion-associated biofilms" refer to biofilms that have corrosive properties which contribute to Microbiologically Influenced Corrosion.

As used herein, the term "pigging" refers to the well-known process of intentional mechanical delamination of corrosion products and biofilm material from the surfaces of metals.

As used herein, the term "corrosion" refers to the general deterioration of a material (e.g., metallic material) due to its reaction with the environment.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein in the specification and the claim can be modified by the term "about."

Any compositions or methods provided herein can be combined with one or more of any of the other compositions and methods provided herein.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims.

Biofilms and MIC

The methods of the present disclosure involve the treatment and mitigation of MIC, which is primarily caused by corrosion-causing biofilms. It will be appreciated that microorganisms present in aqueous environments form biofilms on solid surfaces. Biofilm consists of populations of microorganisms and their hydrated polymeric secretions and, in the case of corrosive biofilms, of inorganic biogenic deposits (such as iron sulfide). Numerous types of organisms may exist in any particular biofilm, ranging from strictly aerobic bacteria at the water interface to anaerobic bacteria such as sulfate-reducing bacteria (SRB) at the oxygen depleted metal surface. Biofilm formation is thought to follow a multi-series of specific steps that include: (a) an initial bacterial attachment stage that is rapid and reversible; (b) a longer term attachment stage; (c) a replication phase; (d) a polysaccharide-rich matrix secretion stage; (e) a biofilm maturation stage; and (f) finally bacterial dispersal stage. Biofilms can be microns to millimeters to centimeters or more in thickness and can develop over the course of hours, days, or months, depending on many factors that include the consortium of bacteria present and the environment. Biofilms are highly complex naturally occurring biotic structures having a wide range of characteristics and their exact role in corrosion is still under intense study. However, biofilm-associated corrosion is at least a function of the composition of the underlying bacterial population that forms the biofilm and on the environment. See Jack (2010) and Enning & Garrelfs (2014)

The presence of biofilm can contribute to corrosion in at least three ways: (1) physical deposition leading to differential concentration cells, (2) production of corrosive metabolic by-products, and (3) deplorization of the metal caused by biochemical reaction (electron uptake).

Many of the byproducts of microbial metabolism including organic acids and hydrogen sulphide are corrosive. These materials can concentrate in the biofilm causing accelerated metal attack.

Biofilms are usually found on solid substrates submerged in or exposed to an aqueous solution, although they can form as floating mats on liquid surfaces and also on the surface of leaves, particularly in high humidity climates. Given sufficient resources for growth, a biofilm will quickly grow to be macroscopic (visible to the naked eye). Biofilms can contain many different types of microorganism, e.g., bacteria, archaea, protozoa, fungi and algae; each group performs specialized metabolic functions. However, some organisms will form single-species films under certain conditions. The social structure (cooperation, competition) within a biofilm highly depends on the different species present.

Biofilms are held together and protected by a matrix of secreted polymeric compounds called EPS. EPS is an abbreviation for either extracellular polymeric substance or exopolysaccharide, although the latter one only refers to the polysaccharide moiety of EPS. In fact, the EPS matrix consists not only of polysaccharides but also of proteins (which may be the major component in environmental and waste water biofilms) and nucleic acids. A large proportion of the EPS is more or less strongly hydrated, however, hydrophobic EPS also occur. This matrix encases the cells within it and facilitates communication among them through biochemical signals as well as gene exchange. The EPS matrix is an important key to the evolutionary success of biofilms and their resistance to, in this case, biocides and other chemical treatments to remove them. One reason is that it traps extracellular enzymes and keeps them in close proximity to the cells. Thus, the matrix represents an external digestion system and allows for stable synergistic microconsortia of different species (Wingender and Flemming, Nat. Rev. Microbiol. 8, 623-633). Some biofilms have been found to contain water channels that help distribute nutrients and signaling molecules. Additionally, corrosive biofilms tend to accumulate a variety of inorganic deposits such as iron sulfides and iron carbonates which can further impact on biocide performance.

The MIC mitigation methods disclosed herein can be used to treat any affected surface, and in particular, any affected metal surface on any equipment involved in the storage, transport, and/or refinery of petroleum and/or natural gas products. For example, affected surfaces can include pipeline that transports crude oil from onshore or offshore production site to local or distant petroleum and/or natural gas refineries. Problematic biofilms can form along the 3.0 interior surfaces of pipelines over distances that extend over many miles or tens of miles, leading to corrosive conditions over a multitude of points. It is generally accepted that pipeline corrosion represents the majority of corrosive damage due to MIC in the oil and gas industries, particularly given that there are over 190,000 miles of liquid pipelines in the US alone. In another example, affected surfaces can include oil storage facilities at refinery sites or those located on oil transport tankers. Other equipment, such as pumps, valves, and other equipment that comes into contact with the oil flow path is susceptible to the formation of biofilms and thus to MIC. Any and all of these sites and surfaces may be treated using the methods disclosed herein.

MIC Mitigation

The disclosure relates to the findings that certain correlations exist between physical parameters, such as, temperature, pH, and flow rate, as well as biological parameters, such as, cell biomass and the microbial community composition, and the existence of conditions that are suitable or which reliably correlate with the formation of MIC. Based on these findings, the inventors have devised a multi-phase process for conditionally treating MIC by evaluating whether MIC-correlating conditions exist, the degree of MIC, if present, and then applying concomitant MIC-mitigating treatment scheme which adjusted in its degree of aggressiveness in proportion to MIC severity. The disclosed methodology allows, in part, for the continuous monitoring and assessment of MIC risk in petroleum-based equipment (e.g., pipeline) and the administering of a treatment that corresponds to the level of severity of the MIC. The methodology also provides for continuous or periodic assessment to evaluate the effectiveness of said treatments, and whether reductions and/or increases in the aggressiveness of the treatment are required. The schemes described herein provide for selective MIC management which in turn results in more effective and targeted solutions with significant costs savings.

As a result of the herein processes, a mitigation treatment is administered for mitigating or eliminating MIC of a metal surface. In certain embodiment, the treatment can comprise contacting a metal surface with an effective amount of a liquid composition comprising a MIC mitigating substance (e.g., a biocide). In another aspect, the disclosure relates to a method for reducing or preventing the formation or activity of a corrosion-associated biofilm on a metal surface comprising contacting the metal surface with an effective amount of a liquid composition comprising a MIC mitigating substance (e.g., a biocide).

The methods disclosed herein may also include testing frameworks that facilitate knowing whether and how to administer a MIC mitigation treatment. Such treating frameworks may aim to determine whether a target system has a legitimate MIC risk at a particular site (e.g., crude pipeline that transports crude oil from an offshore rig to an onshore processing facility). Other steps may also involve subsequent monitoring steps to evaluate the extent of the MIC associated biofilm, and followed then by steps to carry out a particular treatment plan, e.g., an aggressive treatment plan or a lower-strength treatment plan, or to adjust existing plans to either increase or decrease a treatment program based on the whether a certain initial treatment is effective.

For example, corrosive damage to a pipeline might be detected as a result of regularly scheduled maintenance along a certain ten-mile stretch of crude oil pipeline. In order to learn more about the extent and nature of the damage, and therefore, an appropriate treatment, a user might sample the environmental conditions at various points along the pipeline by assessing properties that would be indicative of conditions suitable for biofilm formation, such as, (a) detection of certain bacterial species known to have a role in bacterial corrosion (e.g., sulfate reducing bacteria), (b) detection of certain corrosive metabolites (e.g., presence of organic acids, hydrogen sulfide gas, (c) existence of suitable pH and temperature conditions known to be supportive of biofilm development, (d) presence of an aqueous environment (e.g., extent of water drop-out or separation of a water phase from the crude oil), (e) slow flow rate (slower flow rates are more conducive to biofilm formation), and (f) existence of high bacterial biomass. The skilled person may also wish to examine physical samples collected from the pipeline wall to detect and characterize the biofilm (e.g., thickness) or metal coupon samples placed into the flow path. Such factors can be evaluated and then assessed by the skilled person to design a specifically tailored MIC mitigation treatment.

In some embodiments, variables affecting the specific nature of any given MIC-mitigation treatment can include, for example: (a) pH of a MIC mitigation substance (e.g., biocide), (b) salinity of the MIC mitigation substance, (c) concentration of the MIC mitigation substance in the composition (e.g., 1%, 2%, 5%, 10%, 50%, w/v), (d) target or desired concentration of the MIC mitigation substance once delivered in the flow path (e.g., 1 ppm, 2 ppm, 4 ppm, 10 ppm, 50 ppm, 100 ppm, 500 ppm, 1000 ppm or more), (e) the rate of crude oil flow, (f) the rate of injection of the MIC mitigation substance, (g) the types of bacteria present in the consortium of the biofilm, (h) the level of bacterial biomass and/or biofilm present, (i) the presence of visible evidence of corrosion (e.g., pits) ( ), (j) and the detection of metal loss on test coupons. Each of these factors can be assessed, along with other available factors, to gauge the severity of the MIC risk and/or the degree of biofilm-associated corrosion. Once the severity of the corrosion is known, the skilled person can determine the best course for administering the treatment.

Treatment may be aggressive in nature, or otherwise less aggressive, depending on the degree and severity of the MIC and/or biofilm formation. For example, if the degree of biofilm-associated corrosion is determined to be low, a gentle treatment may be administered by, for example, reducing the total amount or concentration of MIC mitigation substance delivered, reducing the number of hours of continued injection into the site of interest, or increasing the number of days spanning between follow-up injections. However, if the degree of biofilm-associated corrosion is determined to be high, a more aggressive treatment may be administered by, for example, increasing the total amount or concentration of MIC mitigation substance delivered, increasing the time period for continuous injection, increasing the frequency of administration, or shortening the number of time or days between successive treatments.

In one embodiment, a MIC mitigation framework for assessing and treating MIC is provided, said framework comprising: (a) measuring at least one parameter predictive of MIC-forming conditions, (b) determining the level of severity of existing MIC, and (c) administering a concomitant MIC mitigation treatment that is proportional to the level of MIC severity.

The at least one parameter predictive of MIC-forming conditions can be selected from the group consisting of temperature, pH, flow rate, water drop-out, planktonic cell count, and microbial composition. In some cases, two or more parameters are tested, one of which is temperature.

The inventors have found that a temperature that is below about 60° C. is predictive of MIC-forming conditions. In other embodiments, a temperature that is below about 70° C., or more preferably that is below about 80° C., or more preferable that is lower that about 90° C. is predictive of MIC-forming conditions. A temperature between about 20-40° C. is also predictive of MIC-forming conditions.

The disclosure also relates to temperatures which are predictive of non-MIC forming conditions. In some embodiments, a temperature that is above about 60° C. correlates with conditions that do not support MIC. In yet other embodiments, a temperature that is above about 80° C. correlates with conditions that do not support MIC. In still other embodiments, a temperature that is above about 90° C. correlates with conditions that do not support MIC.

Any number of MIC-predictive parameters can be tested. In certain embodiments, at least two, or three, or four, or five, or six, or seven, or more parameters are tested, one of which may be the quantity of bacterial biomass present. The biomass can be measured as the quantity or concentration of planktonic bacteria. The biomass can also be measured as the quantity or concentration or density of bacteria in a biofilm. The biomass can be measured by any known means, such as by quantitative PCR, ATP (adenosine triphosphate) assay, or serial dilution technique (SD). In certain embodiments, the biomass is measured in terms of microbial equivalents (ME, which is comparable to cell numbers). In some embodiments, the MIC-forming conditions require at least $5 \times 10^5$ microbial equivalents per $cm^2$ of biofilm. In other embodiments, MIC-forming conditions require at least $1 \times 10^3$ cells per ml (planktonic cell counts) as measured by ATP assay or qPCR, or at least $1 \times 10^2$ cells per ml (planktonic cell counts) as measured by SD assay.

In certain other embodiments, the level of severity of existing MIC is monitored by measuring the quantity of biofilm biomass and/or observing the metal surfaces (e.g., in situ or of test coupons) for evidence of corrosion (e.g., visible pitting) and corrosion-related debris.

In certain embodiments, the level of severity of existing MIC is lowest (i.e., level 1 severity) when the biofilm biomass is lower than a threshold, wherein the threshold can be $1 \times 10^2$ cells per $cm^2$, $1 \times 10^3$ cells per $cm^2$, or $1 \times 10^4$ cells per $cm^2$. Preferably, the threshold is $1 \times 10^4$ cells per $cm^4$ when the biomass is determined by ATP assay or quantitative PCR, but can be $1 \times 10^2$ cells per $cm^2$ when the biomass is determined by SD assay.

In other embodiments, the severity is increased (i.e., level 2) if the quantity of biofilm biomass is above the threshold but there are no visible signs of localized corrosion (e.g., no visible pitting on in situ components or on coupons).

In still other embodiments, the severity is increased yet again (i.e., level 3) if the quantity of biofilm is above the threshold, and there are visible signs of localized corrosion (e.g., visible pitting on in situ components or on coupons), but the measured level of corrosion on coupons is less than 1 milli-inch per year (<1 mpy).

In still further embodiments, the severity is increased still again (i.e., level 4) if the quantity of biofilm is above the threshold, and there are visible signs of localized corrosion (e.g., visible pitting on in situ components or on coupons), and the measured level of corrosion on coupons is more than 1 milli-inch per year (>1 mpy), but there is no evidence of visible corrosion-related debris.

In still another embodiment, the severity is increased yet again (i.e., level 5) if the quantity of biofilm is above the threshold, and there are visible signs of localized corrosion (e.g., visible pitting on in situ components or on coupons), and the measured level of corrosion on coupons is more than 1 milli-inch per year (>1 mpy), and there is evidence of visible corrosion-related debris.

In accordance with the second aspect, the disclosed method further involves (c) administering a concomitant MIC mitigation treatment that is proportional to the level of MIC severity. Preferably, as the severity of the MIC is increased, the degree of aggressiveness of the MIC treatment is also increased. It is also contemplated, however, that at least between 2 or more levels of severity, the degree of aggressiveness of the MIC treatment is not increased, or is increased only marginally.

In certain embodiments, the treatment is a first-level treatment (lowest level or degree of aggressiveness) comprising administering a biocide to provide a final concentration at the site of interest of 5-1000 ppm over the course of 10 minutes to 10 hours every 14-28 days in combination with pigging at least twice per year. These parameters can be adjusted as needed to adjust the level of aggressiveness. For example, the final concentration (ppm) of the biocide may be adjusted, or the frequencing of injection, or the number of hours of continuous injection, or the frequencing of pigging.

In other embodiments, the treatment is a second-level treatment comprising administering a biocide to provide a final concentration at the site of interest of 5-1000 ppm over the course of 10 minutes to 10 hours every 7-14 days in combination with pigging every 4-8 weeks. These parameters can be adjusted as needed to adjust the level of aggressiveness. For example, the final concentration (ppm) of the biocide may be adjusted, or the frequencing of injection, or the number of hours of continuous injection, or the frequencing of pigging.

In still other embodiments, the treatment is a third-level treatment comprising administering a biocide to provide a final concentration at the site of interest of 5-1000 ppm over the course of 10 minutes to 10 hours every 3-7 days in combination with pigging every 2-4 weeks. These parameters can be adjusted as needed to adjust the level of aggressiveness. For example, the final concentration (ppm) of the biocide may be adjusted, or the frequencing of injection, or the number of hours of continuous injection, or the frequencing of pigging.

In still further embodiments, the treatment is a fourth-level treatment comprising administering a biocide to provide a final concentration at the site of interest of 5-1000 ppm over the course of 10 minutes to 10 hours every 3-7 days in combination with pigging every week. These parameters can be adjusted as needed to adjust the level of aggressiveness. For example, the final concentration (ppm) of the biocide may be adjusted, or the frequencing of injection, or the number of hours of continuous injection, or the frequencing of pigging.

In yet a third aspect, the disclosure relates to a method for selectively mitigating or treating microbiologically influenced corrosion (MIC) of a site of interest comprising:
(a) determining whether suitable conditions for MIC exist at the site of interest;
(b) if so, monitoring the degree of MIC severity at the site of interest;
(c) administering a MIC treatment to the site of interest that corresponds to the degree of MIC severity.

The determining step (a) of the third aspect can comprise measuring the temperature, pH, flow rate, water drop-out, planktonic cell count, and microbial composition to determine whether suitable conditions exist at the site of interest for MIC. In certain embodiments, the determining step includes at least measuring the temperature.

The monitoring step (b) can comprise measuring the biofilm biomass and characterizing the level of corrosion at the site of interest to determine the degree of MIC.

The treatment step can comprise administering a MIC treatment to the site of interest that is proportional to the degree of MIC, wherein the MIC treatment comprises a combination of biocide application and pigging.

In certain embodiments, the determining step (a) can comprise:
(i) measuring the temperature at the site of interest, wherein if the temperature is greater than a threshold temperature, then suitable conditions for MIC do not exist and treatment is not required, but if the temperature is less than the threshold temperature, then proceed to
(ii) measuring the pH at the site of interest, wherein if the pH falls outside a threshold pH range, then suitable conditions for MIC do not exist and treatment is not required, but if the pH falls within a threshold pH range, then proceed to
(iii) measuring the flow rate at the site of interest and the water drop-out, wherein if the flow rate is greater than a threshold flow rate and there is no water drop-out, then suitable conditions for MIC do not exist and treatment is not required, but if the flow rate is less than the threshold flow rate and there is water drop-out, then proceed to
(iv) measuring the planktonic cell count at the site of interest, wherein if planktonic cell count is below a threshold cell count, then suitable conditions for MIC do not exist and treatment is not required, but if the planktonic cell count is above a threshold cell count, then proceed to
(v) determining the microbial community at the site of interest, wherein if less than a threshold percent of the total microbial population comprises species associated with MIC, then suitable conditions for MIC do not exist and treatment is not required, but if more than the threshold percent of the total microbial population comprises species associated with MIC, then proceed to the monitoring step (b) of claim 1 to determine the degree of MIC, and the corresponding treatment of step (c).

In certain embodiments, the threshold temperature of (i) is 60° C.

In certain other embodiments, the threshold temperature of (i) is 90° C.

In certain other embodiments, the threshold temperature is at least 40° C., or at least 45° C., or at least 50° C., or at least 55° C., or at least 60° C., or at least 65° C., or at least 70° C., or at least 75° C., or at least 80° C., or at least 85° C., or at least 90° C., or at least 95° C.

In other embodiment, the threshold pH range of (ii) is a pH of 4-12. In other embodiments, the threshold pH range is a pH of between about 7-8, or between about 6-8, or between about 5-8, or between about 4-8, or between about 3-8, or between about 2-8, or between about 1-8, or between about 4-7, or between about 4-8, or between about 4-9, or between about 4-10, or between about 4-11, or between about 4-12, or between about 4-13, or between about 4-14.

In still other embodiments, the threshold flow rate of (iii) is 10 meters per second (m/s). Alternatively, the threshold flow rate can be at least 1 M/S, or at least 2 m/s, or at least 3 m/s, or at least 4 m/s, or at least 5 m/s, or at least 6 m/s, or at least 7 m/s, or at least 8 m/s, or at least 9 m/s, or at least 10 m/s, or at least 15 m/s, or at least 20 m/s, or at least 50 m/s, or at least 100 m/s or more.

In yet another embodiment, the threshold cell count is $10^3$ cells per ml if the cell count is determined by an ATP assay. In other embodiments, the threshold cell count is $10^2$ cells per ml if the cell count is determined by an SD assay. In still other embodiments, the threshold cell count is $10^3$ cells per ml if the cell count is determined by an qPCR assay. In other embodiments, the cell count threshold is about $10^2$ cells per ml, or $10^3$ cells per ml, or $10^4$ cells per ml, or $10^5$ cells per ml, or $10^6$ cells per ml, or $10^7$ cells per ml, or $10^8$ cells per ml, or $10^9$ cells per ml, or $10^{10}$ cells per ml as measured by any suitable technique for measuring cell count.

In certain embodiments the monitoring step (b) comprises:
(i) measuring the biofilm biomass at the site of interest, wherein if the biofilm biomass is below a threshold biomass, then a first-level MIC treatment is administered to the site of interest, but if the measured biofilm biomass is above the threshold biomass, then proceed to
(ii) investigating the site of interest for localized corrosion, wherein if there is no localized corrosion at the site of interest, then a second-level MIC treatment is administered to the site of interest, but if there localized corrosion, then proceed to
(iii) measuring the level of corrosion of one or more coupons, wherein if the level of corrosion is below a threshold level, then a third-level MIC treatment is administered to the site of interest, but if the level of corrosion is above the threshold level, then proceed to
(iv) detecting the presence of corrosion debris at the site of interest, wherein if no debris is present, then the third-level MIC treatment is administered, but if debris is detected then a fourth-level MIC treatment is administered,
wherein the aggressiveness of the first-level MIC treatment is lower than the second-level MIC treatment, which is lower than the third-level MIC treatment, which is lower than the fourth-level MIC treatment.

In some embodiments, the threshold biomass of (i) is $10^4$ cells/cm$^2$ if measured by an ATP assay, or $10^2$ cells/cm$^2$ if measured by an SD assay, or $10^4$ cells/cm$^2$ if measured by a qPCR assay. In other embodiments, the cell count threshold is about $10^2$ cells per cm$^2$, or $10^3$ cells per cm$^2$, or $10^4$ cells per cm$^2$, or $10^5$ cells per cm$^2$, or $10^6$ cells per cm$^2$, or $10^7$ cells per cm$^2$, or $10^8$ cells per cm$^2$, or $10^9$ cells per cm$^2$, or $10^{10}$ cells per cm$^2$ as measured by any suitable technique for measuring cell count.

In other embodiments, the localized corrosion of (ii) comprises corrosion-related pitting.

In still other embodiments, the threshold level of corrosion of (iii) is 1 milli-inch per year. However, the threshold level of corrosion may be at least 0.1 mpy, or 0.2 mpy, or 0.3 mpy, or 0.4 mpy, or 0.5 mpy, or 0.6 mpy, or 0.7 mpy, or 0.8 mpy, or 0.9 mpy, or 1.0 mpy, or 2.0 mpy, or 3.0 mpy, or 4.0 mpy, or 5.0 mpy, or 6.0 mpy, or 10 mpy, or 20 mpy, or 50 mpy, or more, or any range thereinbetween.

Once the degree of MIC severity is determined, a corresponding MIC treatment may be administered that reflects the level of severity. For example, where MIC severity is the lowest, a first-level treatment can comprise administering a biocide to provide a final concentration at the site of interest of 5-1000 ppm over the course of 10 minutes to 10 hours every 14-28 days in combination with pigging at least twice per year. As the MIC severity is increased, a second-level treatment can comprise administering a biocide to provide a final concentration at the site of interest of 5-1000 ppm over the course of 10 minutes to 10 hours every 7-14 days in combination with pigging every 4-8 weeks. Still, as the severity is further increased, a third-level treatment can comprise administering a biocide to provide a final concentration at the site of interest of 5-1000 ppm over the course of 10 minutes to 10 hours every 3-7 days in combination with pigging every 2-4 weeks. A fourth-level treatment can comprise administering a biocide to provide a final concentration at the site of interest of 5-1000 ppm over the course of 10 minutes to 10 hours every 3-7 days in combination with pigging every week. As described herein, the degree of aggressiveness may be adjusted for each of these levels of treatment by adjusting aspects such as final concentration of biocide, frequency of administration, and level of pigging.

In still other embodiments, the biocides used herein may be provided in a liquid composition having an acidic pH, ranging from about 6.0-7.0, to about 5.5-6.5, to about 4.5-5.5, to about 3.5-4.5, to about 2.5-3.5, to about 1.5-2.5, or lower than 1.5.

In still other embodiments, the biocides used herein may be provided in a liquid composition having an alkaline pH, ranging from about 7.0-7.5, to about 7.5-8.5, to about 8.5-9.5, to about 9.5-10.5, to about 10.5-11.5, to about 11.5-12.5, to about 12.5-13.5 to about 14.

In various embodiments, the effective amount of the liquid composition comprising the disclosed biocides provides a concentration of the biocide that is between about 50-500 micromolar, about 0.5-1.0 mM, about 1.0 mM-5 mM, about 2.5 mM-10 mM, about 5 mM-25 mM, about 10 mM-100 mM, or about 50 mM-1000 mM. As the continuous or periodic monitoring frameworks are implemented, these levels may be adjusted as the severity of MIC changes through the course of treatment.

In various other embodiments, the effective amount of the liquid composition comprising the disclosed biocides provides a final in situ concentration of the biocide at the site of treatment (i.e., which takes into account the flow rate and volume of target solution in order to achieve a final concentration) that is between about 0.1 ppm to 1 ppm, or about 1 ppm to 5 ppm, or about 2.5 ppm to 10 ppm, or about 5 ppm to 20 ppm, or about 10 ppm to 40 ppm, or about 20 ppm to 100 ppm, or about 40 ppm to 500 ppm, or about 100 ppm to 1000 ppm, or about 500 ppm to 10,000 ppm, or more. As the continuous monitoring frameworks are implemented, these levels may be adjusted as the severity of MIC changes through the course of treatment.

In certain other embodiments, the pH of the aqueous environment surrounding or at the metal surface to be treated can be adjusted with buffers or other pH-altering agents to adjust the pH to any basic, neutral, or acidic conditions.

In still other embodiments, the biocides used in the disclosed treatments may be selected from the group consisting of germicides, antibiotics, antibacterials, antivirals, antifungals, antiprotozoals and antiparasites, or combinations thereof.

The biocide used in certain treatments can be selected from the group consisting of germicides, antibiotics, antibacterials, antivirals, antifungals, antiprotozoals and antiparasites.

Combination Treatments

The disclosed treatment methods are also contemplated to be combined with other MIC-mitigation strategies, such as the use of corrosion-resistant metals, temperature control, pH control, radiation, filtration, protective coatings, the use of corrosion inhibitors or other chemical controls (e.g., biocides, oxidizers, acids, alkalis), bacteriological controls (e.g., phages, enzymes, parasitic bacteria, antibodies, competitive microflora), pigging (i.e., mechanical delamination of corrosion products), anodic and cathodic protection, and modulation of nutrient levels.

In particular, in certain embodiments relating to pipeline treatment, the pipeline is first treated with pigging. The pigging can help not only to physically remove MIC-causing biofilms, but also acts to disturb the biofilm such that the permeation of the biofilm is improved, thereby rendering the biocide treatments more effective.

Methods and equipment for pigging lines is well known in the art, and can be found described in the following US patents, each of which are incorporated by reference: U.S. Pat. Nos. 9,010,826; 8,858,732; 8,719,989; 7,739,767; 7,275,564; 6,874,757; 6,182,761; and 6,109,829.

This disclosure is further illustrated by the following examples which should not be construed as limiting. The contents of all references, including any publicly available polypeptide and/or nucleic acid sequences accession numbers (e.g., GenBank), and published patents and patent applications cited throughout the application are hereby incorporated by reference. Those skilled in the art will recognize that the disclosure may be practiced with variations on the disclosed structures, materials, compositions and methods, and such variations are regarded as within the ambit of the disclosure.

EXAMPLES

Example 1: A Method of Selectively Treating Crude Oil Pipeline MIC Based on Monitoring Temperature and Bacterial Biomass Most of crude oil pipeline failure and subsequent replacement can be linked to corrosion caused by microbes. MIC occurs when microbial biofilm attach to the inner walls of oil pipelines causing local consumption of the metal either directly or as a collateral effect of corrosive metabolic by-products (e.g., hydrogen sulfide and/or organic acid). Despite the vast amount of academic knowledge and industrial experience with MIC, the problem is far from being understood. In particular, the complex interactions within mixed microbial communities remain largely unknown.

In an effort to better elucidate and mitigate MIC, the inventors established competencies and knowledge about the physical and chemical parameters affecting and/or influencing MIC. In particular, experiments conducted by the inventors with different samples under a large variety of conditions (temperature, pH, $CO_2$ and $SO_4^{2-}$ concentration, different carbon sources) revealed a constant correlation between temperature and corrosion rates across every sample (data not shown).

At the same time, flow through experiments partially corroborated by field observations, pointed to a positive correlation between bacterial cell numbers and severity of measured corrosion (data not shown).

Finally, the inventors observed that sulfate reducing bacteria from the genus *Desulfovibrio* was a key player for MIC, confirming similar views in the literature.

The instant experiment examined the effects and/or role of temperature and biomass on MIC in crude oil pipeline. Natural microbial communities from a pristine marine soil, as well as 2 produced water samples were enriched anaerobically in batch cultures under sulfate reducing conditions and in the presence of carbon steel. Different carbon sources and, for produced water samples, site-specific crude oils, were used. Negative controls (same conditions, but lacking microbes), were set as well to evaluate background level of non-biological corrosion. For all samples tested, the same temperature-dependency was observed.

MIC strongly affected corrosion rates at temperatures between 20° C. and 40° C. By contrast, MIC was barely detectable over background corrosion levels (i.e., negative control corrosion levels) at 60° C. These results suggest a physiological limitation for microbes causing corrosion at elevated temperatures, and in particular, at temperature at or above 60° C.

With respect to the biomass measurements, biocide lab testing under flow-through systems was coupled with monitoring of bacterial biomass via Adenosine Tri-Phosphate (ATP) quantification (although any accepted method for measuring biomass could be utilized), revealing a cut-off for corrosion at approximately $5 \times 10^5$ microbial equivalent (ME is comparable to cell numbers) per $cm^2$. That is, corrosion did not occur where at ME of less than $5 \times 10^5$. In addition, the MIC-associated bacterial population was assessed by high-throughput DNA sequencing of laboratory samples. It was observed that higher corrosion rates were correlated to a higher relative abundance of the genus *Desulfovibrio* within the microbial community. Thus, sulfate-reducing bacteria were the main contributors of the observed MIC.

Example 2: A Method for Selectively Treating Crude Oil Pipeline MIC Based on Continuous Analysis of a Linear Set of Multiple Parameters A significant fraction of crude oil pipeline failures and subsequent replacement can be linked to corrosion caused by microbes. MIC occurs when microbial biofilm attach to the inner walls of oil pipelines causing local consumption of the metal either directly or as a collateral effect of corrosive metabolic by-products (e.g., hydrogen sulfide and/or organic acid). Despite the vast amount of academic knowledge and industrial experience with MIC, the problem is far from being understood. In particular, the complex interactions within mixed microbial communities remain largely unknown.

In an effort to better elucidate and mitigate MIC, the inventors established competencies and knowledge about the physical and chemical parameters affecting and/or influencing MIC. In particular, experiments conducted by the inventors with different samples under a large variety of conditions (temperature, pH, $CO_2$ and $SO_4^{2-}$ concentration, different carbon sources) revealed a constant correlation between temperature and corrosion rates across every sample (data not shown).

At the same time, flow through experiments partially corroborated by field observations, pointed to a positive correlation between bacterial cell numbers and severity of measured corrosion (data not shown).

Finally, the inventors observed that sulfate reducing bacteria from the genus *Desulfovibrio* was a key player for MIC, confirming similar views in the literature.

The instant experiment examined the effects and/or role of various physical (e.g., temperature, pH, flowrate, water drop-out, coupon corrosion, debris formation) and biological (e.g., planktonic cell count, biofilm bacterial cell count, microbial community) parameters on MIC. A tri-phase framework was established for assessing the risk of MIC formation (phase 1—"MIC ASSESSMENT"), monitoring MIC level/severity once determined to be present in a sample (phase 2—"MIC MONITORING"), and MIC mitigation (phase 3—"MIC MITIGATION"), the aggressiveness of which is a function of MIC severity determined by phase 2.

An exemplary embodiment of this framework is shown in FIG. 1. In an exemplary scenario, one may wish to examine a section of crude oil pipeline for possible MIC and then determine what level or degree of MIC mitigation should be deployed. In this embodiment, the user begins by obtaining one or more samples from the site of interest. The sample may include the fluid contents (i.e., the crude oil flow or any water-phase portion thereof, as well as interior surface biofilm biomass) and any test objects (e.g., metal coupons) that may have been introduced into the site of interest typically used for monitoring corrosion levels.

Under phase (1) (MIC ASSESSMENT), the sample is evaluated by measuring a linear set of successive physical and biological parameters in order to determine whether conditions are suitable for MIC.

Step (1a). Temperature.

In the first step of the MIC ASSESSMENT, the temperature of the sample is measured—or more accurately—the in situ temperature of the sample. Without being bound by theory, the inventors have observed that the risk of MIC is low to none if the temperature of the material being sampled (i.e., the site of the sample) is greater than 90° C. Thus, only conditions having temperature at or below 90° C. are suitable for MIC formation. If the temperature is greater than 90° C., then no further analysis is required, i.e., the user does not need to proceed with the testing. Thus, no further MIC ASSESSMENT testing is performed, and no MIC MONITORING and no MIC MITIGATION steps are performed. However, if the temperature of the in situ sample is at or less than 90° C., then the user advances down the chain of testing to measure the pH of the sample (1b).

Step (1b). pH.

As shown in FIG. 1 at (1b), if the pH of the sample is less than 4 or greater than 12, then no further analysis is required, i.e., the user does not need to proceed with the testing. Thus, no further MIC ASSESSMENT testing is performed, and no MIC MONITORING and no MIC MITIGATION steps are performed. However, if the pH is at or between 4 to 12, then the user advances down the chain of testing to measure the in situ flow rate of the location of the sample and the appearance of water drop-out (1d).

Step (1c-1d). Flow Rate and Water Drop-Out.

As shown in FIG. 1 at (1c and 1d), if the flow rate is greater than 10 m/s (meters per second) and there is no water drop-out, then no further analysis is required, i.e., the user does not need to proceed with the testing. Thus, no further MIC ASSESSMENT testing is performed, and no MIC MONITORING and no MIC MITIGATION steps are performed. However, if the flow rate is at or less than 10 m/s and there is water drop-out, then the user advances down the chain of testing to measure the planktonic cell count at (1e). In addition, since (1c) and (1d) are coupled, both conditions need to be satisfied before moving on to the next step. Thus, if the flow rate is greater than 10 m/s but there is no water drop-out, it would be the case that no further MIC ASSESSMENT is performed. Conversely, if the flow rate is less than 10 m/s but no water drop-out, it would also be the case that no further MIC ASSESSMENT is performed.

Step (1e). Planktonic Cell Count.

In the next step of the MIC ASSESSMENT, the level of planktonic bacteria are measured. Without being bound by theory, the inventors propose that if the level of planktonic cell growth reaches above a certain threshold, then it reflects those conditions that are suitable for MIC formation. Different tests may be used to assess the planktonic growth, including, but not limited to measuring the level of ATP (i.e., ATP assay), the level of SD, and quantitative PCR. At step 1e, if any one of ATP, SD, or qPCR levels are equal to or greater than the indicated threshold level, then the user proceeds to the next step in the assessment. In other words, only one of the ATP, SD, or qPCR metrics needs to be at or over the indicated threshold level of $10^3$ cells/ml, $10^2$ cells/ml, or $10^3$ cells/ml, respectively. Conversely, if each of the ATP, SD, or qPCR levels are below the indicated thresholds, then no further MIC ASSESSMENT testing is performed, and no MIC MONITORING and no MIC MITIGATION steps are performed.

Step (1f). Microbial Community Assessment.

In the last step of the MIC ASSESSMENT phase, the microbial community is characterized by any acceptable means (e.g., antibody detection, qPCR, high-throughput sequencing). If it is found that more than 1% of the total bacterial or archaeal population are the types of microbes identified in the state of the art as being associated with MIC (e.g., SRB, methanogens, acid-producing bacteria), then the user proceeds to phase 2 or the MIC MONITORING phase of the framework. If it is found, however, that 1% or less of the total bacterial/archaeal population are MIC-associated microbes, then no further MIC ASSESSMENT testing is performed, and no MIC MONITORING and no MIC MITIGATION steps are performed.

Under phase (2) (MIC MONITORING), a second level, more detailed evaluation of the sample site is conducted, the results of which drive decision making to determine what level of treatment is performed in phase (3) or the MIC MITIGATION phase.

Step (2a). Biofilm Cell Count.

In this step, the biofilm and/or pig debris contained in the sample is directly evaluated to determine the cell count (or biomass) therein. Different tests may be used to assess the cell count, including, but not limited to measuring the level of ATP (i.e., ATP assay), serial dilution (SD), and quantitative PCR. At step 2a, if any one of ATP, SD, or qPCR levels are equal to or greater than the indicated threshold level, then the user proceeds to the next step in the assessment. In other words, only one of the ATP, SD, or qPCR metrics needs to be at or over the indicated threshold level of $10^4$ cells/cm$^2$, $10^2$ cells/cm$^2$, or $10^4$ cells/cm$^2$, respectively. Conversely, if each of the ATP, SD, or qPCR levels are below the indicated thresholds, then user proceeds to administer the recommended treatment under phase (3), i.e., MIC MITIGATION, and specifically, treatment (3a) (the first-tier level of treatment), i.e., biocide between 5-1000 ppm for 10 min-10 hours, every 14-28 days plus pigging at least twice per year.

Step (2b). Localized Corrosion or Surface Pitting.

Should the next step be reached under MIC MONITORING, the user is then asked to examine the sample—or the sample's in situ site (e.g., pipe wall or a coupon placed in flow path)—to look for visible evidence of localized corrosion, which is typically characterized as surface pitting. If there is no evidence of surface pitting visible at the site, then the user proceeds to administer the indicated treatment of (3b) (the second-tier level of treatment), i.e., biocide administration of between 5-1000 ppm for 10 min-10 hours, every 7-14 days plus pigging every 4-8 weeks. Conversely, if there is evidence of corrosion or surface pitting, then the user proceeds to the next test of measuring coupon corrosion levels.

Step (2c). Coupon Corrosion Levels.

Should the next step be reached under MIC MONITORING, the user is then asked to measure the corrosion levels of metal coupons. The metal coupons can be those placed in situ at the site of sample extraction or they can be coupons allowed to interact in the lab with the sample material. If the level of coupon corrosion measured is less than 1 mpy (milli-inch per year), then the user proceeds to administer the indicated treatment of (3c) (the third-tier level of treatment), i.e., biocide administration of between 5-1000 ppm for 10 min-10 hours, every 3-7 days plus pigging every 2-4 weeks. Conversely, if the coupon corrosion is measured as being greater than 1 mpy, then the user proceeds to the next test of determining whether corrosion debris exists.

Step (2d). Corrosion Debris.

Should the final step be reached under MIC MONITORING, the user is then asked to examine the sample—or the sample's in situ site (e.g., pipe wall or a coupon placed in flow path)—to look for visible evidence of corrosion debris, which is marker of advanced MIC. If there is no evidence debris, then the user proceeds to maintain the indicated treatment of (3c) (the third-tier level of treatment), i.e., biocide administration of between 5-1000 ppm for 10 min-10 hours, every 7-14 days plus pigging every 4-8 weeks. Conversely, if there is evidence of debris corrosion, then the user proceeds to administer the most aggressive level of treatment, i.e., tier-four treatment which involves administering a biocide at between 5-1000 ppm for 10 min-10 hours every 3-7 days plus pigging at least weekly.

The framework also accounts for continuous MIC MONITORING concomitant with ongoing MIC MITIGATION to provide a degree of feedback such that the level of treatment or MIC MITIGATION may be adjusted depending on the reassessment of tests (2a), (2b), (2c), and (2d) as treatment proceeds. The MIC MONITORING can be repeated every 4-30 weeks in one embodiment.

It should be noted that the framework presented in FIG. 1 and described in detail above is not intended to be limiting as other related frameworks and variations thereof are conceivable and within the ambit of the disclosure.

For example, the disclosure contemplates variation frameworks having a different set and/or arrangement of parameters in phase 1 ("MIC ASSESSMENT"). The order of tests of phase 1 depicted in FIG. 1 is temperature>pH>flow and water drop-out>planktonic cell count>microbial community analysis of biofilm and/or pig debris. However, the analysis under phase 1 is envisioned to be rearranged in any number of suitable ways, such as, but not limited to the following:

(d) microbial community analysis>planktonic cell count and water-drop out>flow>pH>temperature;

(e) temperature>pH>flow and water drop-out>planktonic cell count>microbial community analysis of biofilm and/or pig debris;

(f) pH>temperature>flow and water drop-out>planktonic cell count>microbial community analysis of biofilm and/or pig debris;

(g) flow and water drop-out>temperature>pH>planktonic cell count>microbial community analysis of biofilm and/or pig debris;

(h) temperature/pH in any order>flow and water drop-out in any order>planktonic cell count/microbial community analysis in any order;

(i) flow/water drop-out in any order>temperature/pH in any order>planktonic cell count/microbial community analysis in any order; or (j) planktonic cell count/microbial community analysis in any order>temperature/pH in any order>flow/water drop-out in any order.

Other frameworks are contemplated wherein the specific treatments are varied. However, it will generally be the case that the tier-one treatment will be the least aggressive level of treatment, and the tier-four treatment will be the most aggressive level of treatment, and the intermediary treatments will be some where in-between.

Figure 2:
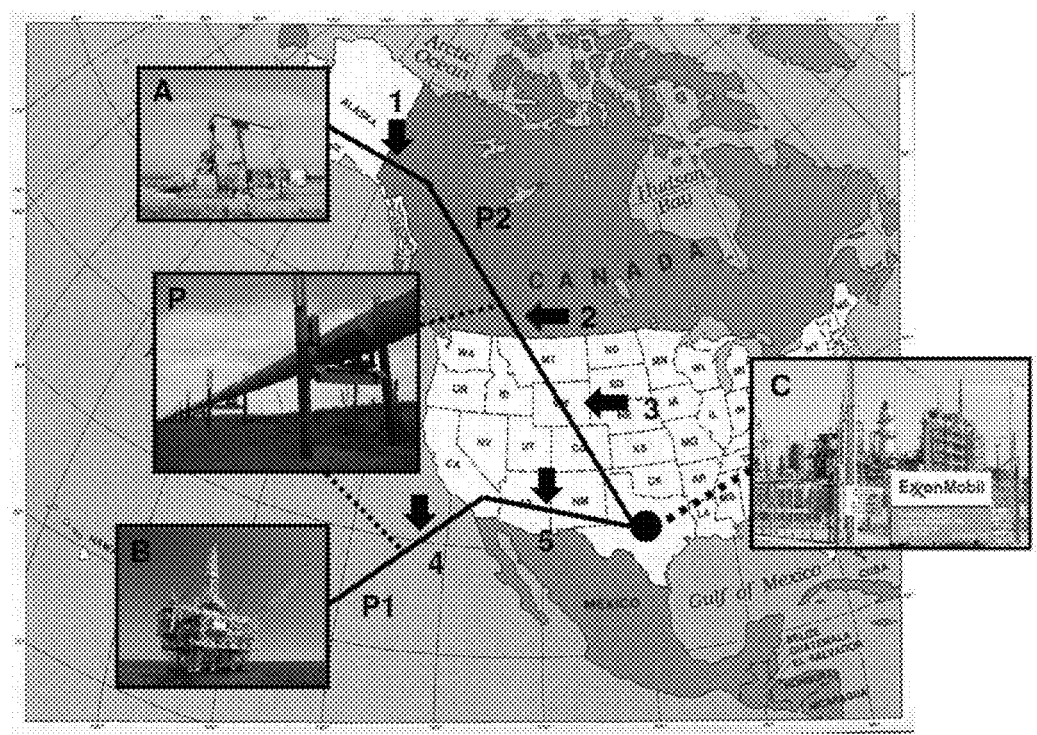
FIG. 2 depicts a hypothetical scenario leads to potential significant costs savings due to ability to selectively conduct MIC mitigation as described herein.

Example 3: Use of Analytical Framework of Example 2 in Hypothetical Scenario Leads to Potential Significant Costs Savings Due to Ability to Selectively Conduct MIC Mitigation FIG. 2 depicts a hypothetical scenario involving (A) an oil field rig in Alaska, (B) an offshore oil drilling rig located off the coast of the U.S., (C) an oil refinery in Texas, and (P) pipeline P1 and P2 which transport crude oil from the Alaskan oil rig and the offshore oil rig to the oil refinery for processing. Along the many thousands of miles of oil pipeline, there exist sampling sites Nos. 1, 2, and 3 at a proximal, intermediate, and distal site of the Alaskan pipeline P2 and sampling sites Nos. 4 and 5 at a proximal and distal portion of the offshore pipeline P1. Applying the framework would first require that a sample is obtained from each of the sites 1-5. Next, each of the samples would be evaluated in accordance with the first phase of the framework, i.e., the MIC ASSESSMENT phase. Thus, a user would test for temperature, pH, flow rate, water drop-out, planktonic cell count, and microbial community in the manner provided in flowpath of the MIC ASSESSMENT phase. If any sample is detected as having conditions suitable for forming MIC, then the user proceeds to the second phase of the framework, i.e., the MIC MONITORING phase. Each applicable sample is tested in accordance with the steps of the MIC MONOTORING phase and depending on the outcome of each test, a level of treatment pursuant to the MIC MITIGATION phase is applied. Following treatment, MIC MONITORING may be repeated every 4-30 weeks.

Since each sample site is tested individually, and only some of the sample sites may show indications of existing MIC, treatment is selective and only necessary for those sample sites requiring treatment under the framework under the optimized treatment regime.

REFERENCES

The following references are incorporated herein by reference:

Lee, W., et al., ROLE OF SULFATE-REDUCING BACTERIA IN CORROSION OF MILD-STEEL—A REVIEW. Biofouling, 1995. 8(3): p. 165;

Paisse, S., et al., Sulfate-reducing bacteria inhabiting natural corrosion deposits from marine steel structures. Applied Microbiology and Biotechnology, 2013. 97(16): p. 7493-750; and Enning, D. and J. Garrelfs, Corrosion of Iron by Sulfate-Reducing Bacteria: New Views of an Old Problem. Applied and Environmental Microbiology, 2014. 80(4): p. 1226-1236.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:

1. A method for selectively mitigating Microbial Influenced Corrosion (MIC) of a site of interest comprising:
   (a) determining whether suitable conditions for MIC exist at the site of interest;
   (b) if so, monitoring the degree of MIC severity at the site of interest;
   (c) administering an MIC treatment to the site of interest that corresponds to the degree of MIC severity;
   wherein the determining step (a) comprises:
   (i) measuring the temperature at the site of interest, wherein if the temperature is greater than a threshold temperature, then suitable conditions for MIC do not exist and treatment is not required, but if the temperature is less than the threshold temperature, then proceed to
   (ii) measuring the pH at the site of interest, wherein if the pH falls outside a threshold pH range, then suitable conditions for MIC do not exist and treatment is not required, but if the pH falls within a threshold pH range, then proceed to
   (iii) measuring the flow rate at the site of interest and the water drop-out, wherein if the flow rate is greater than a threshold flow rate and there is no water drop-out, then suitable conditions for MIC do not exist and treatment is not required, but if the flow rate is less than the threshold flow rate and there is water drop-out, then proceed to (iv) measuring the planktonic cell count at the site of interest, wherein if planktonic cell count is below a threshold cell count, then suitable conditions for MIC do not exist and treatment is not required, but if the planktonic cell count is above a threshold cell count, then proceed to (v) determining the microbial community at the site of interest, wherein if less than a threshold percent of the total microbial population comprises species associated with MIC, then suitable conditions for MIC do not exist and treatment is not required, but if more than the threshold percent of the total microbial population comprises species associated with MIC, then proceed to the monitoring step (b) to determine the degree of MIC, and the corresponding treatment of step (c), and wherein the monitoring step (b) comprises:

(i) measuring the biofilm biomass at the site of interest, wherein if the biofilm biomass is below a threshold biomass, then a first-level MIC treatment is administered to the site of interest, but if the measured biofilm biomass is above the threshold biomass, then proceed to (ii) detecting the site of interest for localized corrosion, wherein if there is no localized corrosion at the site of interest, then a second-level MIC treatment is administered to the site of interest, but if there is localized corrosion, then proceed to (iii) measuring the level of corrosion of one or more coupons, wherein if the level of corrosion is below a threshold level, then a third-level MIC treatment is administered to the site of interest, but if the level of corrosion is above the threshold level, then proceed to (iv) detecting the presence of corrosion debris at the site of interest, wherein if no debris is present, then the third-level MIC treatment is administered, but if debris is detected then a fourth-level MIC treatment is administered, wherein the aggressiveness of the first-level MIC treatment is lower than the second-level MIC treatment, which is lower than the third-level MIC treatment, which is lower than the fourth-level MIC treatment.

2. The method of claim 1, wherein for the administering step (c) the MIC treatment comprises a combination of biocide application and pigging.

3. The method of claim 1, wherein the threshold temperature of (i) is 60° C.

4. The method of claim 1, wherein the threshold temperature of (i) is 90° C.

5. The method of claim 1, wherein the threshold pH range of (ii) is a pH of 4-12.

6. The method of claim 1, wherein the threshold flow rate of (iii) is 10 meters per second (m/s).

7. The method of claim 1, wherein the threshold cell count is $10^3$ cells per ml if the cell count is determined by an ATP assay.

8. The method of claim 1, wherein the threshold cell count is $10^2$ cells per ml if the cell count is determined by an SD assay.

9. The method of claim 1, wherein the threshold cell count is $10^3$ cells per ml if the cell count is determined by an qPCR assay.

10. The method of claim 1, wherein the threshold biomass of (i) is $10^4$ cells/cm$^2$ if measured by an ATP assay, or $10^2$ cells/cm$^2$ if measured by an SD assay, or $10^4$ cells/cm$^2$ if measured by a qPCR assay.

11. The method of claim 1, wherein the localized corrosion of (ii) comprises corrosion-related pitting.

12. The method of claim 1, wherein the threshold level of corrosion of (iii) is 1 milli-inch per year.

13. The method of claim 1, wherein the first-level treatment comprises administering a biocide to provide a final concentration at the site of interest of 5-1000 ppm over the course of 10 minutes to 10 hours every 14-28 days in combination with pigging at least twice per year.

14. The method of claim 1, wherein the second-level treatment comprises administering a biocide to provide a final concentration at the site of interest of 5-1000 ppm over the course of 10 minutes to 10 hours every 7-14 days in combination with pigging every 4-8 weeks.

15. The method of claim 1, wherein the third-level treatment comprises administering a biocide to provide a final concentration at the site of interest of 5-1000 ppm over the course of 10 minutes to 10 hours every 3-7 days in combination with pigging every 2-4 weeks.

16. The method of claim 1, wherein the fourth-level treatment comprises administering a biocide to provide a final concentration at the site of interest of 5-1000 ppm over the course of 10 minutes to 10 hours every 3-7 days in combination with pigging every week.

17. The method of claim 1, wherein the MIC is caused by a bacterial biofilm deposited on the surface of the site of interest.

18. The method of claim 17, wherein the bacterial biofilm is formed by anaerobic bacteria.

19. The method of claim 18, wherein the anaerobic bacteria are selected from the group consisting of sulfate reducing bacteria, iron oxidizing bacteria, sulfur oxidizing bacteria, nitrate reducing bacteria, methanogens, and acid producing bacteria.

20. The method of claim 19, wherein the sulfate reducing bacteria is of the genera *Desulfuvibrio, Desulfotomaculum, Desulfosporomusa, Desulfosporosinus, Desulfobacter, Desulfobacterium, Desulfobacula, Desulfobotulus, Desulfocella, Desulfococcus, Desulfofaba, Desulfofrigus, Desulfonema, Desulfosarcina, Desulfospira, Desulfotalea, Desulfotignum, Desulfobulbus, Desulfocapsa, Desulfofustis, Desulforhopalis, Desulfoarculus, Desulfobacca, Desulfomonile, Desulfotigmum, Desulfohalobium, Desulfomonas, Desulfonatronovibrio, Desulfomicrobium, Desulfonatronum, Desulfacinum, Desulforhabdus, Syntrophobacter, Syntrophothermus, Thermaerobacter*, and *Thermodesulforhabdus*.

21. The method of claim 20, wherein the sulfate reducing bacteria is of the genera *Desulfuvibrio*.

22. The method of claim 1, wherein the site of interest is a metal surface of equipment for refining, storing, or transporting of crude or processed oil.

23. The method of claim 1, wherein the the site of interest is a metal surface of equipment for refining, storing, or transporting of natural gas.

24. The method of claim 1, wherein the biocide is selected from the group consisting of germicides, antibiotics, antibacterials, antivirals, antifungals, antiprotozoals and antiparasites.

25. The method of claim 1, further comprising a secondary treatment for mitigating or eliminating MIC selected from the group consisting of pigging, radiation treatment, pH adjustment, nutrient adjustment, and installation of corrosion-resistant metals.

* * * * *